US009492629B2

(12) United States Patent
Sanchez et al.

(10) Patent No.: US 9,492,629 B2
(45) Date of Patent: Nov. 15, 2016

(54) METHODS AND SYSTEMS FOR VENTILATION WITH UNKNOWN EXHALATION FLOW AND EXHALATION PRESSURE

(71) Applicants: Gabriel Sanchez, Valley Center, CA (US); Richard Nakai, Long Beach, CA (US); Danis Carter, Escondido, CA (US); Nancy Dong, Carlsbad, CA (US)

(72) Inventors: Gabriel Sanchez, Valley Center, CA (US); Richard Nakai, Long Beach, CA (US); Danis Carter, Escondido, CA (US); Nancy Dong, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 13/767,750

(22) Filed: Feb. 14, 2013

(65) Prior Publication Data
US 2014/0224250 A1    Aug. 14, 2014

(51) Int. Cl.
*A61M 16/00* (2006.01)
*A61M 16/20* (2006.01)
*A61M 16/16* (2006.01)

(52) U.S. Cl.
CPC ....... *A61M 16/204* (2014.02); *A61M 16/0051* (2013.01); *A61M 16/205* (2014.02); *A61M 16/0063* (2014.02); *A61M 16/161* (2014.02); *A61M 2016/0027* (2013.01); *A61M 2016/0039* (2013.01); *A61M 2016/0042* (2013.01); *A61M 2205/16* (2013.01); *A61M 2205/17* (2013.01); *A61M 2205/3368* (2013.01); *A61M 2205/505* (2013.01)

(58) Field of Classification Search
CPC .................. A61M 2230/205; A61M 16/0051; A61M 2205/18; A61M 2230/435; A61M 2205/16; A61M 16/205; A61M 16/204; A61M 2205/17; A61M 2016/0015; A61M 2016/0039; A61M 2016/0042; A61M 2016/0027; A61M 2016/0036; A61B 5/0008; G06F 19/3406; G06F 19/3431
USPC ............ 128/203.14, 204.21, 204.23, 200.24, 128/202.22, 203.12, 204.18, 204.26, 205.24
See application file for complete search history.

(56) References Cited

U.S. PATENT DOCUMENTS

| 3,827,433 | A | 8/1974 | Shannon |
| 3,869,771 | A | 3/1975 | Bollinger |
| 3,889,670 | A | 6/1975 | Loveland et al. |
| 3,896,800 | A | 7/1975 | Cibulka |

(Continued)

FOREIGN PATENT DOCUMENTS

WO            03055552         7/2003

OTHER PUBLICATIONS

Hari (Flow Sensor Fault Causing Ventilator Malfunction, Anaesthesia, 2005, 60, pp. 1042-2052; http://onlinelibrary.wiley.com/doi/10.1111/j.1365-2044.2005.04396.x/pdf; Accessed Jan. 16, 2015).*

(Continued)

*Primary Examiner* — Peter S Vasat (57) ABSTRACT

This disclosure describes systems and methods for providing novel back-up ventilation. Further, this disclosure describes systems and methods for delivering ventilation when exhalation pressure and/or exhalation flow are unknown or unreliable by the ventilator.

19 Claims, 5 Drawing Sheets

(56) References Cited

U.S. PATENT DOCUMENTS

| | | |
|---|---|---|
| 3,908,987 A | 9/1975 | Boehringer |
| 3,976,065 A | 8/1976 | Durkan |
| 4,020,834 A | 5/1977 | Bird |
| 4,050,458 A | 9/1977 | Friend |
| 4,057,059 A | 11/1977 | Reid, Jr. et al. |
| 4,082,093 A | 4/1978 | Fry et al. |
| 4,155,357 A | 5/1979 | Dahl |
| 4,197,843 A | 4/1980 | Bird |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,245,633 A | 1/1981 | Erceg |
| 4,265,237 A | 5/1981 | Schwanbom et al. |
| 4,267,827 A | 5/1981 | Racher et al. |
| 4,285,340 A | 8/1981 | Gezari et al. |
| 4,320,754 A | 3/1982 | Watson et al. |
| 4,323,064 A | 4/1982 | Hoenig et al. |
| 4,351,328 A | 9/1982 | Bodai |
| 4,351,329 A | 9/1982 | Ellestad et al. |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,596,246 A | 6/1986 | Lyall |
| 4,598,706 A | 7/1986 | Darowski et al. |
| 4,611,591 A | 9/1986 | Inui et al. |
| 4,622,976 A | 11/1986 | Timpe et al. |
| 4,651,731 A | 3/1987 | Vicenzi et al. |
| 4,752,089 A | 6/1988 | Carter |
| 4,813,409 A | 3/1989 | Ismach |
| 4,821,709 A | 4/1989 | Jensen |
| 4,877,023 A | 10/1989 | Zalkin |
| 4,921,642 A | 5/1990 | LaTorraca |
| 4,924,862 A | 5/1990 | Levinson |
| 4,954,799 A | 9/1990 | Kumar |
| 5,002,050 A | 3/1991 | McGinnis |
| 5,007,420 A | 4/1991 | Bird |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,737 A | 12/1991 | Goulding |
| 5,150,291 A | 9/1992 | Cummings et al. |
| 5,158,569 A | 10/1992 | Strickland et al. |
| 5,161,525 A | 11/1992 | Kimm et al. |
| 5,165,398 A | 11/1992 | Bird |
| 5,222,491 A | 6/1993 | Thomas |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,698 A | 4/1994 | Tobia et al. |
| 5,315,989 A | 5/1994 | Tobia |
| 5,319,540 A | 6/1994 | Isaza et al. |
| 5,323,772 A | 6/1994 | Linden et al. |
| 5,325,861 A | 7/1994 | Goulding |
| 5,333,606 A | 8/1994 | Schneider et al. |
| 5,335,651 A | 8/1994 | Foster et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,487,383 A | 1/1996 | Levinson |
| 5,494,028 A | 2/1996 | DeVries et al. |
| 5,507,282 A | 4/1996 | Younes |
| 5,509,406 A | 4/1996 | Kock et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power et al. |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,419 A | 9/1996 | Froehlich et al. |
| 5,575,283 A | 11/1996 | Sjoestrand |
| 5,582,163 A | 12/1996 | Bonassa |
| 5,596,984 A | 1/1997 | O'Mahoney et al. |
| 5,606,968 A | 3/1997 | Mang |
| 5,615,669 A | 4/1997 | Olsson et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,647,345 A | 7/1997 | Saul |
| 5,647,351 A | 7/1997 | Weismann et al. |
| 5,651,360 A | 7/1997 | Tobia |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,694,926 A | 12/1997 | DeVries et al. |
| 5,715,812 A | 2/1998 | Deighan et al. |
| 5,730,122 A | 3/1998 | Lurie |
| 5,735,267 A | 4/1998 | Tobia |
| 5,740,796 A | 4/1998 | Skog |
| 5,752,509 A | 5/1998 | Lachmann et al. |
| 5,762,480 A | 6/1998 | Adahan |
| 5,769,072 A | 6/1998 | Olsson et al. |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,868,133 A | 2/1999 | DeVries et al. |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,970,975 A | 10/1999 | Estes et al. |
| 5,975,081 A | 11/1999 | Hood et al. |
| 5,983,891 A | 11/1999 | Fukunaga |
| 6,000,396 A | 12/1999 | Melker et al. |
| 6,003,513 A | 12/1999 | Readey et al. |
| 6,010,459 A | 1/2000 | Silkoff et al. |
| 6,024,089 A | 2/2000 | Wallace et al. |

(56) References Cited

U.S. PATENT DOCUMENTS

| | | |
|---|---|---|
| 6,029,664 A | 2/2000 | Zdrojkowski et al. |
| 6,029,667 A | 2/2000 | Lurie |
| 6,041,780 A | 3/2000 | Richard et al. |
| 6,042,550 A | 3/2000 | Haryadi et al. |
| 6,047,860 A | 4/2000 | Sanders |
| 6,067,984 A | 5/2000 | Piper |
| 6,076,523 A | 6/2000 | Jones et al. |
| 6,095,139 A | 8/2000 | Psaros |
| 6,095,140 A | 8/2000 | Poon et al. |
| 6,102,038 A | 8/2000 | DeVries |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,674 A | 9/2000 | Rich |
| 6,135,106 A | 10/2000 | Dirks et al. |
| 6,142,150 A | 11/2000 | O'Mahoney |
| 6,148,814 A | 11/2000 | Clemmer et al. |
| 6,152,132 A | 11/2000 | Psaros |
| 6,158,432 A | 12/2000 | Biondi et al. |
| 6,161,539 A | 12/2000 | Winter |
| 6,192,885 B1 | 2/2001 | Jalde |
| 6,200,271 B1 | 3/2001 | Kuck et al. |
| 6,210,342 B1 | 4/2001 | Kuck et al. |
| 6,213,119 B1 | 4/2001 | Brydon et al. |
| 6,217,524 B1 | 4/2001 | Orr et al. |
| 6,220,244 B1 | 4/2001 | McLaughlin |
| 6,220,245 B1 | 4/2001 | Takabayashi et al. |
| 6,238,351 B1 | 5/2001 | Orr et al. |
| 6,241,681 B1 | 6/2001 | Haryadi et al. |
| 6,258,038 B1 | 7/2001 | Haryadi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,305,374 B1 | 10/2001 | Zdrojkowski et al. |
| 6,306,098 B1 | 10/2001 | Orr et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,427,692 B1 | 8/2002 | Hoglund |
| 6,439,229 B1 | 8/2002 | Du et al. |
| 6,443,154 B1 | 9/2002 | Jalde et al. |
| 6,450,968 B1 | 9/2002 | Wallen et al. |
| 6,467,477 B1 | 10/2002 | Frank et al. |
| 6,467,478 B1 | 10/2002 | Merrick et al. |
| 6,510,846 B1 | 1/2003 | O'Rourke |
| 6,512,938 B2 * | 1/2003 | Claure et al. ............... 600/323 |
| 6,526,970 B2 | 3/2003 | DeVries et al. |
| 6,532,957 B2 | 3/2003 | Berthon-Jones |
| 6,532,960 B1 | 3/2003 | Yurko |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,557,553 B1 | 5/2003 | Borrello |
| 6,560,991 B1 | 5/2003 | Kotliar |
| 6,564,798 B1 | 5/2003 | Jalde |
| 6,568,387 B2 | 5/2003 | Davenport et al. |
| 6,571,795 B2 | 6/2003 | Bourdon |
| 6,584,973 B1 | 7/2003 | Biondi et al. |
| 6,588,422 B1 | 7/2003 | Berthon-Jones et al. |
| 6,609,517 B1 | 8/2003 | Estes et al. |
| 6,626,175 B2 | 9/2003 | Jafari et al. |
| 6,640,806 B2 | 11/2003 | Yurko |
| 6,644,310 B1 | 11/2003 | Delache et al. |
| 6,659,100 B2 | 12/2003 | O'Rourke |
| 6,662,032 B1 | 12/2003 | Gavish et al. |
| 6,668,824 B1 | 12/2003 | Isaza et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,705,314 B1 | 3/2004 | O'Dea |
| 6,718,974 B1 | 4/2004 | Moberg |
| 6,725,447 B1 | 4/2004 | Gilman et al. |
| 6,739,337 B2 | 5/2004 | Isaza |
| 6,752,151 B2 | 6/2004 | Hill |
| 6,758,216 B1 | 7/2004 | Berthon-Jones et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg et al. |
| 6,786,216 B2 | 9/2004 | O'Rourke |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,848,444 B2 | 2/2005 | Smith et al. |
| 6,854,462 B2 | 2/2005 | Berthon-Jones et al. |
| 6,866,040 B1 | 3/2005 | Bourdon |
| 6,877,511 B2 | 4/2005 | DeVries et al. |
| 6,899,103 B1 | 5/2005 | Hood et al. |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 6,986,349 B2 | 1/2006 | Lurie |
| 6,990,980 B2 | 1/2006 | Richey, II |
| 7,000,612 B2 | 2/2006 | Jafari et al. |
| 7,032,589 B2 | 4/2006 | Kerechanin, II et al. |
| 7,036,504 B2 | 5/2006 | Wallace et al. |
| 7,040,318 B2 | 5/2006 | Däscher et al. |
| 7,056,334 B2 | 6/2006 | Lennox |
| 7,066,177 B2 | 6/2006 | Pittaway et al. |
| 7,077,131 B2 | 7/2006 | Hansen |
| 7,080,646 B2 | 7/2006 | Wiesmann et al. |
| RE39,225 E | 8/2006 | Isaza et al. |
| 7,096,866 B2 | 8/2006 | Be'eri et al. |
| 7,117,438 B2 | 10/2006 | Wallace et al. |
| 7,121,277 B2 | 10/2006 | Ström |
| 7,122,010 B2 | 10/2006 | Böhm et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,156,095 B2 | 1/2007 | Melker et al. |
| 7,204,251 B2 | 4/2007 | Lurie |
| 7,219,666 B2 | 5/2007 | Friberg et al. |
| 7,246,618 B2 | 7/2007 | Habashi |
| 7,255,103 B2 | 8/2007 | Bassin |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,278,962 B2 | 10/2007 | Lönneker-Lammers |
| 7,290,544 B1 | 11/2007 | Särelä et al. |
| 7,296,573 B2 | 11/2007 | Estes et al. |
| 7,308,894 B2 * | 12/2007 | Hickle .................. 128/204.23 |
| 7,320,321 B2 | 1/2008 | Pranger et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,465,275 B2 | 12/2008 | Stenqvist |
| 7,472,702 B2 | 1/2009 | Beck et al. |
| 7,478,634 B2 | 1/2009 | Jam |
| 7,481,222 B2 | 1/2009 | Reissmann |
| 7,487,773 B2 | 2/2009 | Li |
| 7,487,778 B2 | 2/2009 | Freitag |
| 7,527,058 B2 | 5/2009 | Wright et al. |
| RE40,814 E | 6/2009 | Van Brunt et al. |
| 7,556,041 B2 | 7/2009 | Madsen |
| 7,562,657 B2 | 7/2009 | Blanch et al. |
| 7,574,368 B2 | 8/2009 | Pawlikowski et al. |
| 7,581,708 B2 | 9/2009 | Newkirk |
| 7,588,033 B2 | 9/2009 | Wondka |
| 7,617,824 B2 | 11/2009 | Doyle |
| 7,621,270 B2 | 11/2009 | Morris et al. |
| 7,628,151 B2 | 12/2009 | Bassin |
| 7,644,713 B2 | 1/2010 | Berthon-Jones |

(56) References Cited

U.S. PATENT DOCUMENTS

| | | |
|---|---|---|
| 7,654,802 B2 | 2/2010 | Crawford, Jr. et al. |
| 7,672,720 B2 | 3/2010 | Heath |
| 7,686,019 B2 | 3/2010 | Weiss et al. |
| 7,694,677 B2 | 4/2010 | Tang |
| 7,708,015 B2 | 5/2010 | Seeger et al. |
| 7,717,113 B2 | 5/2010 | Andrieux |
| 7,717,858 B2 | 5/2010 | Massad |
| 7,721,736 B2 | 5/2010 | Urias et al. |
| D618,356 S | 6/2010 | Ross |
| 7,730,884 B2 | 6/2010 | Sato et al. |
| 7,735,492 B2 | 6/2010 | Doshi et al. |
| 7,784,461 B2 | 8/2010 | Figueiredo et al. |
| 7,793,656 B2 | 9/2010 | Johnson |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,823,588 B2 | 11/2010 | Hansen |
| 7,841,347 B2 | 11/2010 | Sonnenschein et al. |
| 7,849,854 B2 | 12/2010 | DeVries et al. |
| 7,855,716 B2 | 12/2010 | McCreary et al. |
| D632,796 S | 2/2011 | Ross et al. |
| D632,797 S | 2/2011 | Ross et al. |
| 7,886,739 B2 | 2/2011 | Soliman et al. |
| 7,891,354 B2 | 2/2011 | Farbarik |
| 7,893,560 B2 | 2/2011 | Carter |
| 7,909,034 B2 | 3/2011 | Sinderby et al. |
| D638,852 S | 5/2011 | Skidmore et al. |
| 7,938,114 B2 | 5/2011 | Matthews et al. |
| 7,971,589 B2 | 7/2011 | Mashak et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 8,844,526 B2 | 9/2014 | Jafari et al. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2002/0017301 A1 | 2/2002 | Lundin |
| 2002/0026941 A1 | 3/2002 | Biondi et al. |
| 2002/0117173 A1 | 8/2002 | Lynn et al. |
| 2002/0144681 A1 | 10/2002 | Cewers et al. |
| 2003/0029453 A1 | 2/2003 | Smith et al. |
| 2003/0140925 A1 | 7/2003 | Sapienza et al. |
| 2003/0168066 A1* | 9/2003 | Sallvin ............... 128/204.21 |
| 2003/0172929 A1* | 9/2003 | Muellner ............ 128/204.18 |
| 2003/0225339 A1 | 12/2003 | Orr et al. |
| 2005/0034724 A1 | 2/2005 | O'Dea |
| 2005/0034727 A1 | 2/2005 | Shusterman et al. |
| 2005/0039748 A1 | 2/2005 | Andrieux |
| 2005/0113668 A1 | 5/2005 | Srinivasan |
| 2005/0139212 A1 | 6/2005 | Bourdon |
| 2005/0166928 A1 | 8/2005 | Jiang |
| 2005/0247311 A1 | 11/2005 | Vacchiano et al. |
| 2006/0249153 A1 | 11/2006 | DeVries et al. |
| 2006/0264762 A1 | 11/2006 | Starr |
| 2006/0272637 A1 | 12/2006 | Johnson |
| 2006/0283451 A1 | 12/2006 | Albertelli |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0056588 A1 | 3/2007 | Hayek |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0089741 A1 | 4/2007 | Bohm et al. |
| 2007/0125377 A1 | 6/2007 | Heinonen et al. |
| 2007/0227537 A1 | 10/2007 | Bemister et al. |
| 2007/0272241 A1 | 11/2007 | Sanborn et al. |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0011296 A1 | 1/2008 | Schatzl |
| 2008/0021379 A1 | 1/2008 | Hickle |
| 2008/0041383 A1 | 2/2008 | Matthews et al. |
| 2008/0045845 A1 | 2/2008 | Pfeiffer et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0110461 A1 | 5/2008 | Mulqueeny et al. |
| 2008/0135044 A1 | 6/2008 | Freitag et al. |
| 2008/0168990 A1 | 7/2008 | Cooke et al. |
| 2008/0178874 A1 | 7/2008 | Doshi et al. |
| 2008/0183057 A1 | 7/2008 | Taube |
| 2008/0196720 A1 | 8/2008 | Kollmeyer et al. |
| 2008/0200775 A1 | 8/2008 | Lynn |
| 2008/0202528 A1 | 8/2008 | Carter et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0312519 A1 | 12/2008 | Maschke |
| 2008/0314385 A1 | 12/2008 | Brunner et al. |
| 2009/0007914 A1 | 1/2009 | Bateman |
| 2009/0020119 A1 | 1/2009 | Eger et al. |
| 2009/0071478 A1 | 3/2009 | Kalfon |
| 2009/0090359 A1 | 4/2009 | Daviet et al. |
| 2009/0099621 A1 | 4/2009 | Lin et al. |
| 2009/0107982 A1 | 4/2009 | McGhin et al. |
| 2009/0114223 A1 | 5/2009 | Bonassa |
| 2009/0137919 A1 | 5/2009 | Bar-Lavie et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1* | 7/2009 | Cong ............... A61B 5/091 128/204.23 |
| 2009/0171176 A1 | 7/2009 | Andersohn |
| 2009/0183739 A1 | 7/2009 | Wondka |

(56) References Cited

U.S. PATENT DOCUMENTS

| | | |
|---|---|---|
| 2009/0194109 A1 | 8/2009 | Doshi et al. |
| 2009/0205661 A1 | 8/2009 | Stephenson et al. |
| 2009/0205663 A1 | 8/2009 | Vandine et al. |
| 2009/0210032 A1 | 8/2009 | Beiski et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250058 A1 | 10/2009 | Lastow et al. |
| 2009/0260625 A1 | 10/2009 | Wondka |
| 2009/0266360 A1 | 10/2009 | Acker et al. |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0299155 A1 | 12/2009 | Yang et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308394 A1 | 12/2009 | Levi |
| 2009/0308398 A1 | 12/2009 | Ferdinand et al. |
| 2009/0314297 A1 | 12/2009 | Mathews |
| 2010/0011307 A1 | 1/2010 | Desfossez et al. |
| 2010/0016694 A1 | 1/2010 | Martin et al. |
| 2010/0018531 A1 | 1/2010 | Bassin |
| 2010/0024818 A1 | 2/2010 | Stenzler et al. |
| 2010/0024820 A1 | 2/2010 | Bourdon |
| 2010/0031443 A1 | 2/2010 | Georgiev et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen et al. |
| 2010/0078024 A1* | 4/2010 | Andrieux .......... A61M 16/0051 128/204.21 |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0094366 A1 | 4/2010 | McCarthy |
| 2010/0101575 A1 | 4/2010 | Fedorko et al. |
| 2010/0108066 A1 | 5/2010 | Martin et al. |
| 2010/0108070 A1 | 5/2010 | Kwok |
| 2010/0114218 A1 | 5/2010 | Heath |
| 2010/0116270 A1 | 5/2010 | Edwards et al. |
| 2010/0125227 A1 | 5/2010 | Bird |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0148458 A1 | 6/2010 | Ross et al. |
| 2010/0175695 A1 | 7/2010 | Jamison |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252046 A1 | 10/2010 | Dahlström et al. |
| 2010/0275920 A1 | 11/2010 | Tham et al. |
| 2010/0275921 A1 | 11/2010 | Schindhelm et al. |
| 2010/0282259 A1 | 11/2010 | Figueiredo et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0307507 A1 | 12/2010 | Li et al. |
| 2010/0319691 A1 | 12/2010 | Lurie et al. |
| 2010/0326442 A1 | 12/2010 | Hamilton et al. |
| 2010/0326447 A1 | 12/2010 | Loomas et al. |
| 2010/0331877 A1 | 12/2010 | Li et al. |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0023875 A1 | 2/2011 | Ledwith |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0061650 A1 | 3/2011 | Heesch |
| 2011/0073112 A1 | 3/2011 | DiBlasi et al. |
| 2011/0088697 A1 | 4/2011 | DeVries et al. |
| 2011/0100365 A1 | 5/2011 | Wedler et al. |
| 2011/0108041 A1 | 5/2011 | Sather et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209706 A1 | 9/2011 | Truschel et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |

(56) References Cited

U.S. PATENT DOCUMENTS

| | | |
|---|---|---|
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0251328 A1 | 9/2014 | Graboi et al. |
| 2014/0261409 A1 * | 9/2014 | Dong et al. .............. 128/202.22 |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0114115 A1 | 4/2016 | Glenn et al. |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

METHODS AND SYSTEMS FOR VENTILATION WITH UNKNOWN EXHALATION FLOW AND EXHALATION PRESSURE

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes.

Ventilation with Unknown Exhalation Flow and Exhalation Pressure

This disclosure describes systems and methods for providing novel enhanced back-up ventilation. Further, this disclosure describes systems and methods for delivering ventilation when exhalation flow and/or exhalation pressure is unknown or unreliable by the ventilator.

In part, this disclosure describes a method for ventilating a patient with a ventilator. The method includes:

a) monitoring inspiratory flow, inspiratory pressure, expiratory flow, and expiratory pressure during ventilation of a patient with a ventilator;

b) delivering a ventilation based at least on the expiratory flow and the expiratory pressure;

c) determining a malfunction that makes at least one of the expiratory flow and the expiratory pressure unreliable; and d) in response to the malfunction, ceasing delivering ventilation based at least on the expiratory flow and the expiratory pressure and delivering ventilation based on at least one of the inspiratory flow and the inspiratory pressure.

Yet another aspect of this disclosure describes a ventilator system that includes: a pressure generating system; a ventilation tubing system; an exhalation valve; a plurality of sensors; a main driver; a backup driver; and a controller. The pressure generating system is adapted to generate a flow of breathing gas. The ventilation tubing system includes a patient interface for connecting the pressure generating system to a patient. The exhalation valve is connected to the ventilation tubing system. The plurality of sensors are operatively coupled to at least one of the pressure generating system, the patient, and the ventilation tubing system for monitoring inspiratory pressure, inspiratory flow, exhalation pressure, and exhalation flow. The main driver controls the exhalation valve during ventilation to deliver a pressure to a patient based at least on the exhalation pressure and the exhalation flow monitored by the plurality of sensors. The backup driver controls the exhalation valve to deliver the pressure to the patient during ventilation based on the inhalation pressure and the inhalation flow monitored by the plurality of sensors. The controller determines a malfunction that makes the expiratory flow and the expiratory pressure unreliable and switches from the main driver to the backup driver.

The disclosure further describes a computer-readable medium having computer-executable instructions for performing a method for ventilating a patient with a ventilator. The method includes:

a) repeatedly monitoring inspiratory flow, inspiratory pressure, expiratory flow, and expiratory pressure during ventilation of a patient with a ventilator;

b) repeatedly delivering a ventilation based at least on the expiratory flow and the expiratory pressure;

c) determining a malfunction that makes at least one of the expiratory flow and the expiratory pressure unreliable; and d) in response to the malfunction, ceasing delivering ventilation based at least on the expiratory flow and the expiratory pressure and delivering ventilation based on at least one of the inspiratory flow and the inspiratory pressure.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist/control ventilation modes. Assist control modes allow a spontaneously breathing patient to trigger inspiration during ventilation.

In the event of malfunctions and/or system failures in ventilators, most ventilators sound an alarm and stop ventilation or potentially enter a passive state. Ventilators stop ventilation because the necessary devices or systems for delivering the desired ventilation are unreliable or undeterminable based on the malfunction.

For example, the ventilator utilizes several systems and/or components to control the pressure of gas delivered to the patient, such as the source of gas, the inspiratory conduit and valve, the inspiratory module, expiratory conduit and valve, and an expiratory module. The expiratory module utilizes measured expiratory flow and/or expiratory pressure to control the exhalation valve to deliver the desired amount of flow and/or pressure during inspiration and exhalation. For example, the exhalation module controls the exhalation valve to establish pressure during the inhalation phase and to create the Positive End-Expiratory Pressure (PEEP) during the exhalation phase. If expiratory flow and/or expiratory pressure are unavailable, the ventilator is unable to determine the pressure level to apply to the patient and therefore ceases ventilation.

However, it is desirable to provide ventilation to a patient whose ability to breathe on his or her own is impaired. Accordingly, the systems and methods disclosed herein provide ventilation in the event that exhalation pressure and/or exhalation flow are undeterminable or unreliable. The terms unreliable and undeterminable as used herein, while having different meanings, are utilized interchangeably in this disclosure. Accordingly, the term "unreliable" encompasses the term "undeterminable" and the term "undeterminable" encompasses "unreliable." Under fault conditions or during a malfunction of the expiratory system, the expiratory flow sensor, the expiratory pressure sensor, and control of the valve are unreliable. Therefore, expiratory flow, expiratory pressure, valve position, valve current, valve current command, and valve dampening command are unreliable. When exhalation flow and/or exhalation pressure are undeterminable, a desired pressure may be established by the ventilator by deriving parameters and/or signals from the inspiratory flow and/or inspiratory pressure.

An example of a fault condition is presented by the Exhalation Back-Up Ventilation (EBUV) mode under which the data measurement and acquisition subsystem on the exhalation side of the ventilator is deactivated because of a malfunction. As discussed above, conventional ventilators declare an alarm and terminate ventilation. However, the EBUV mode allows a ventilator to continue ventilating the patient under such conditions until an appropriate substitute device is made available.

Accordingly, the systems and methods described herein provide the desired amount of pressure to a patient during ventilation by controlling an exhalation valve based on monitored inspiratory pressure and inspiratory flow. In some embodiments, the exhalation valve is controlled by a backup driver separate from a main driver. In further embodiments, the backup driver is on a circuit isolated from the main driver.

Figure 1A:
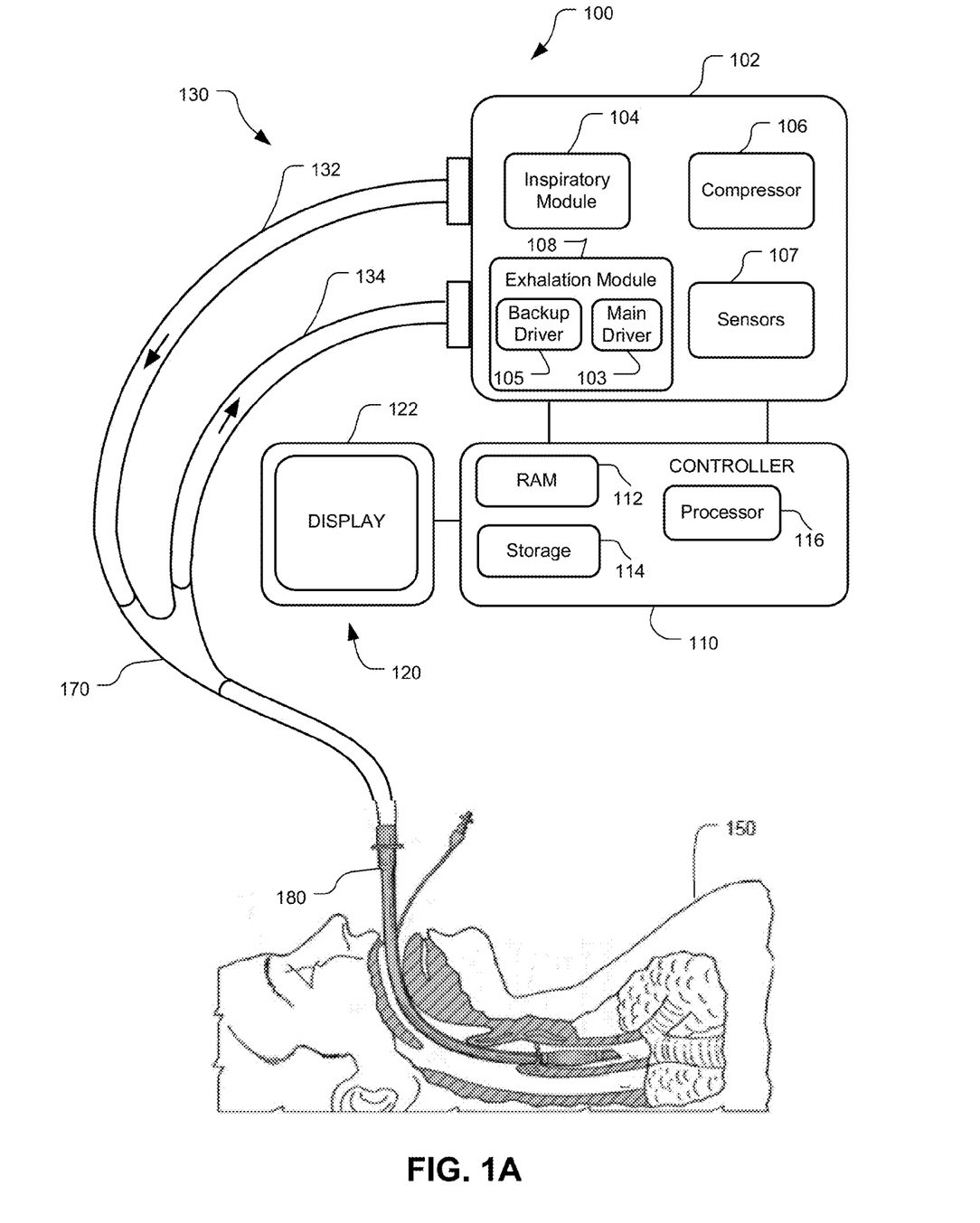
FIG. 1A illustrates an embodiment of a ventilator.
Figure 1B:
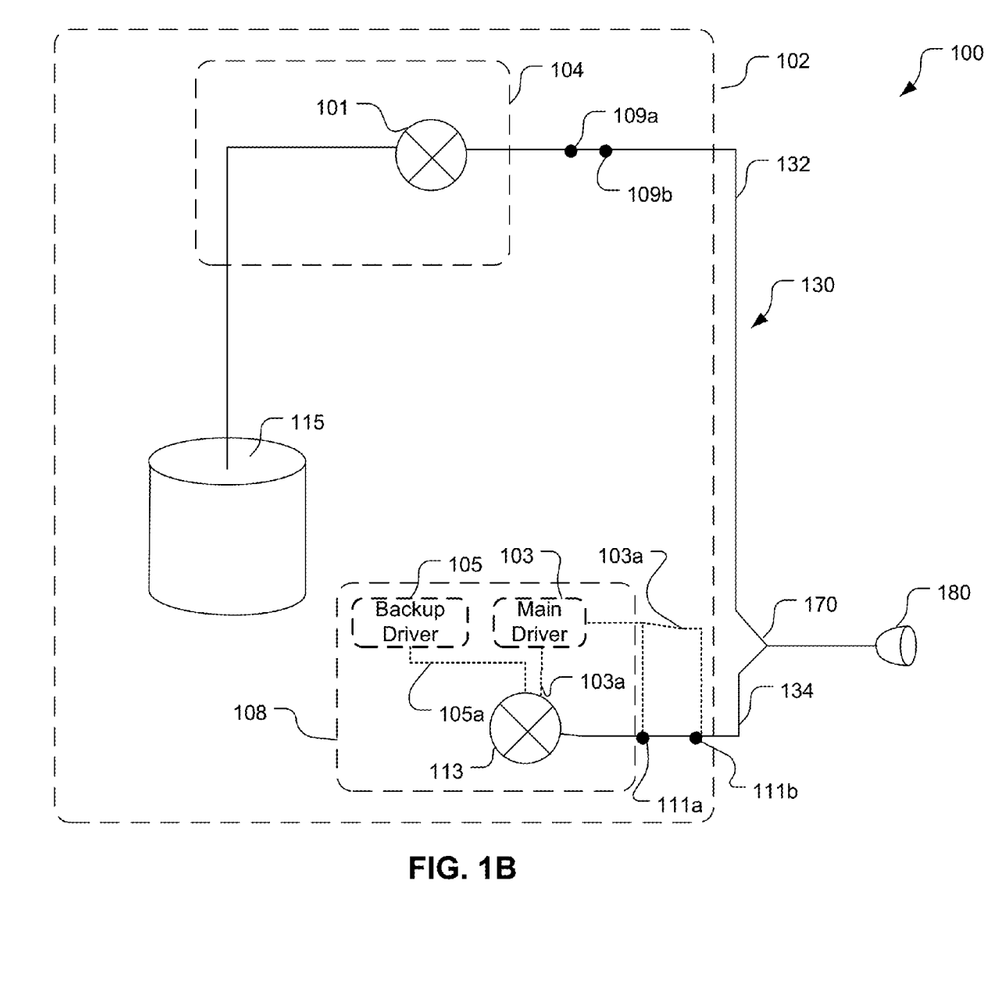
FIG. 1B illustrates an embodiment of the ventilator shown in FIG. 1A.

FIGS. 1A and 1B are diagrams illustrating an embodiment of an exemplary ventilator 100. The exemplary ventilator 100 illustrated in FIG. 1A is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180. The pneumatic system 102 delivers ventilation to the patient 150 according to predetermined or selected modes (spontaneous, assist, mandatory, etc.) and breath types (pressure control, pressure support, pressure assist, volume control, volume support, volume-controlled-pressure-targeted, etc.).

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an exhalation limb 134 of the ventilation tubing system 130.

Pneumatic system 102 may be configured in a variety of ways. In the present example, pneumatic system 102 includes an exhalation module 108 coupled with the exhalation limb 134 and an inspiratory module 104 coupled with the inspiratory limb 132. Compressor 106, accumulator 115 (as illustrated in FIG. 1B) and/or other source(s) of pressurized gases (e.g., air, oxygen, and/or helium) is coupled with inspiratory module 104 and the exhalation module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory delivery valve 101 for controlling gas delivery to the patient 150 and/or gas delivery through the inspiratory limb 132 as illustrated in FIG. 1B. In some embodiments, inspiratory module 104 is configured to provide ventilation according to various ventilator modes, such as mandatory and assist modes.

The exhalation module 108 is configured to release gases from the patient's lungs and/or exhalation circuit according to prescribed ventilatory settings. Accordingly, the exhalation module 108 also controls gas delivery through the inspiratory limb 132 and the exhalation limb 134. The exhalation module 108 controls an exhalation valve 113 which regulates the flow of gases from the patient's lungs and/or exhalation circuit according to prescribed ventilatory settings.

As illustrated in FIG. 1B, the exhalation module 108 includes a main driver 103 for controlling the exhalation valve 113. The main driver 103 controls the exhalation valve 113 to establish pressure during inhalation to the desired inspiration pressure. Further, the main driver 103 controls the exhalation valve 113 to establish the desired PEEP during exhalation. The main driver 103 utilizes a control algorithm that is computed by utilizing monitored exhalation pressure and monitored exhalation flow. The monitored exhalation flow and/or pressure are determined by one or more sensors 107, which are discussed in further detail below.

In some embodiments, the main driver 103 is a differential driver. In other embodiments, the main driver 103 is pulse width modulation driver. The above listed drivers are not meant to be limiting. Any suitable driver for controlling an exhalation module 108 in a ventilator may be utilized by the ventilator 100.

Further, as illustrated in FIG. 1B, the exhalation module 108 includes a backup driver 105 for controlling the exhalation valve 113. The exhalation module 108 utilizes a backup driver 105 when a malfunction in the expiratory system is detected by the controller 110. The detected malfunction may include a malfunction of the main driver 103. The malfunction prevents the expiratory flow and/or expiratory pressure from being determined.

The backup driver 105 controls the exhalation valve 113 to establish pressure during inhalation to the desired inspiration pressure. Further, the backup driver 105 controls the exhalation valve 113 to establish the desired PEEP during exhalation. Because the expiratory pressure is not determinable, the amount of PEEP delivered is determined based on the monitored inspiration pressure and monitored inspiration flow during a malfunction. The backup driver 105 utilizes an inspiration control algorithm to deliver the desired inspiration pressure that is computed by utilizing monitored inspiration pressure and monitored inspiration flow. The backup driver 105 utilizes an exhalation control algorithm to deliver the PEEP that is computed by utilizing monitored inspiration pressure and monitored inspiration flow. In some embodiments, the exhalation control algorithm subtracts the measured inspiration pressure from the desired PEEP. The monitored exhalation flow and/or pressure are determined by one or more sensors 107, which are discussed in further detail below.

In some embodiments, as illustrated in FIG. 1B the backup driver 105 is on a backup circuit 105a that is separated from or isolated from the main driver 103 and the main driver circuit 103a. The main driver circuit 103a of the main driver 103 is connected to the exhalation valve 113 and one or more expiratory sensors, such as an expiratory flow sensor 111a and an expiratory pressure sensor 111b as illustrated in FIG. 1B. In this embodiment, the backup driver 105 is on a separate backup circuit 105a that connects the backup driver 105 to the exhalation valve 113 and is separated/isolated from an exhalation sensor (exhalation pressure sensor 111b and/or exhalation flow sensor 111a) and/or the main driver 103. A separate backup driver 105 and an isolated backup circuit 105a for the backup driver 105 allow the backup driver 105 to function regardless of a malfunctioning exhalation sensor and/or a malfunctioning main driver 103.

In some embodiments, the backup driver 103 is a pulse modulated driver. In other embodiments, the backup driver 105 is pulse width modulation driver. The above listed drivers are not meant to be limiting. Any suitable driver for controlling an exhalation module 108 in a ventilator may be utilized by the ventilator 100.

The ventilator 100 also includes a plurality of sensors 107 communicatively coupled to ventilator 100. The sensors 107 may be located in the pneumatic system 102, ventilation tubing system 130, and/or on the patient 150. The embodiment of FIG. 1A illustrates a plurality of sensors 107 in pneumatic system 102.

Sensors 107 may communicate with various components of ventilator 100, e.g., pneumatic system 102, other sensors 107, exhalation module 108, inspiratory module 104, processor 116, controller 110, and any other suitable components and/or modules. In one embodiment, sensors 107 generate output and send this output to pneumatic system 102, other sensors 107, exhalation module 108, inspiratory module 104, processor 116, controller 110, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or exhalation triggering effort, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or exhalation modules 104, 108 for detecting changes in, for example, inspiratory flow, inspiratory pressure, expiratory pressure, and expiratory flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Any sensory device useful for monitoring changes in measurable parameters during ventilatory treatment may be employed in accordance with embodiments described herein.

For example, in some embodiments, the one or more sensors 107 of the ventilator 100 include an inspiratory flow sensor 109a and an exhalation flow sensor 111a as illustrated in FIG. 1B. In one embodiment, the inspiratory flow sensor 109a is located in the inspiratory limb 132 and is controlled by the inspiratory module 104. However, the inspiratory flow sensor 109a may be located in any suitable position for monitoring inspiratory flow and may be monitored by any suitable ventilator component, such as a pressure generating system 102. In one embodiment, the exhalation flow sensor 111a is located in the exhalation limb 134 and is monitored by the exhalation module 108. However, the exhalation flow sensor 111a may be located in any suitable position for monitoring exhalation flow and may be monitored by any suitable ventilator component, such as a pressure generating system 102.

Further, in some embodiments, the one or more sensors 107 of the ventilator 100 also include an inspiratory pressure sensor 109b and/or an exhalation pressure sensor 111b as illustrated in FIG. 1B. In one embodiment, the inspiratory pressure sensor 109b is located in the inspiratory limb 132 and is controlled by the inspiratory module 104. However, the inspiratory pressure sensor 109b may be located in any suitable position for monitoring inspiratory pressure and may be monitored by any suitable ventilator component, such as a pressure generating system 102. In one embodiment, the exhalation pressure sensor 111b is located in the exhalation limb 134 and is monitored by the exhalation module 108. However, the exhalation pressure sensor 111b may be located in any suitable position for monitoring exhalation pressure and may be monitored by any suitable ventilator component, such as a pressure generating system 102.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships. For example, in some embodiments, inspiration flow is derived from measured inspiration pressure and vice versa. In another example, exhalation pressure is derived from exhalation flow and vice versa.

The pneumatic system 102 may include a variety of other components, including mixing modules, valves, tubing, accumulators 115, filters, etc. For example, FIG. 1B illustrates the use of an accumulator 115.

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate the use of EBUV mode during a malfunction and/or any other information known, received, or stored by the ventilator 100.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In some embodiments, controller 110 includes memory 112, one or more processors 116, storage 114, and/or other components of the type commonly found in command and control computing devices, as illustrated in FIG. 1A. In alternative embodiments, the controller 110 is separate component from the operator interface 120 and pneumatic system 102. In other embodiments, the controller 110 is located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Further, controller 110 determines if there is a malfunction that makes exhalation flow and/or exhalation pressure undeterminable. Accordingly, the controller 110 determines if the exhalation flow sensor 111a, exhalation pressure sensor 111b, and/or the valve command (i.e., the main driver 103) are unreliable. If the exhalation flow sensor 111a, exhalation pressure sensor 111b, and/or the valve command are determined to be unreliable by the controller 110, then the monitored expiratory flow, monitored expiratory pressure, valve position, valve current, valve current command, valve dampening command, and etc. may all be unreliable.

Several different systems and method are currently utilized and known in the art for determining a malfunction in the exhalation module 108 and components of the exhalation module (e.g., the exhalation flow sensor 111a, exhalation pressure sensor 111b, and/or the valve command (i.e., the main driver 103)). The controller 110 detects a malfunction utilizing any of these known systems or methods. For example, malfunctions may be detected based on changes in voltages, temperatures, wattages, coefficients, humidity, and/or overcurrent for various components (e.g., exhalation flow sensor 111a, exhalation valve 113, and/or main driver 103) of the exhalation module 108.

If the controller 110 detects a malfunction, the controller 110 communicates with the exhalation module 108 and instructs the exhalation module 108 to switch to a backup driver 105. Further, the controller 110 instructs the pneumatic system 102 to enter EBUV mode of ventilation. The EBUV mode is a pressure targeted mandatory mode of ventilation. The pressure to be administered to a patient 150 during inspiration and exhalation of the mandatory breath is determined by the ventilator 100. Further, the inspiratory time, and respiratory rate for a patient 150 are also predetermined by the ventilator 100. These variables determine the breath profile to be delivered to the patient 150 during each mandatory breath inspiration and expiration. The mandatory breaths are administered according to the predetermined respiratory rate. For the EBUV mode, when the inspiratory time is equal to the prescribed inspiratory time, the ventilator 100 initiates exhalation. Exhalation lasts from the end of inspiration until the next inspiration. Upon the end of exhalation, another mandatory breath is given to the patient 150.

During an EBUV mode, the ventilator 100 delivers a repeating pressure waveform, regardless of variations in lung or airway characteristics, e.g., respiratory compliance and/or respiratory resistance. However, the volume and flow waveforms may fluctuate based on lung and airway characteristics. In some embodiments, the ventilator 100 determines the set pressure (including the inspiratory pressure and the PEEP), the inspiratory time, and respiration rate based on known ventilator parameters that have not been corrupted by the determined malfunction, such as weight, height, sex, age, and disease state. In other embodiments, the set pressure (including the inspiratory pressure and the PEEP), the inspiratory time, and the respiration rate are predetermined by the ventilator 100 upon the detection of a malfunction and are the same for any patient 150 being ventilated by the ventilator 100.

If the controller 110 does not determine a malfunction, the controller 110 does not send instructions to the exhalation module 108 and the exhalation module 108 continues to control the exhalation valve 113 utilizing a main driver 103. In some embodiments, the controller 110 is part of the exhalation module 108. In some embodiments, the controller 110 is part of the pneumatic system 102.

Additionally, controller 110 determines if the ventilator 100 is in an inspiratory phase (delivering inspiration) or an expiratory phase (delivering exhalation) of breath during ventilation based on the mandatory mode of ventilation after a malfunction is determined. The ventilator 100 delivers inspiration and exhalation automatically based on the set breath rate. Accordingly, the ventilator 100 determines the inspiration and exhalation phases. If the controller 110 determines that the ventilator 100 is in the inspiration phase of the breath, the pressure delivered to the patient 150 is a set inspiration pressure. If the controller 110 determines that the ventilator 100 is in the exhalation phase of the breath, the pressure delivered to the patient 150 is a set PEEP.

Figure 2:
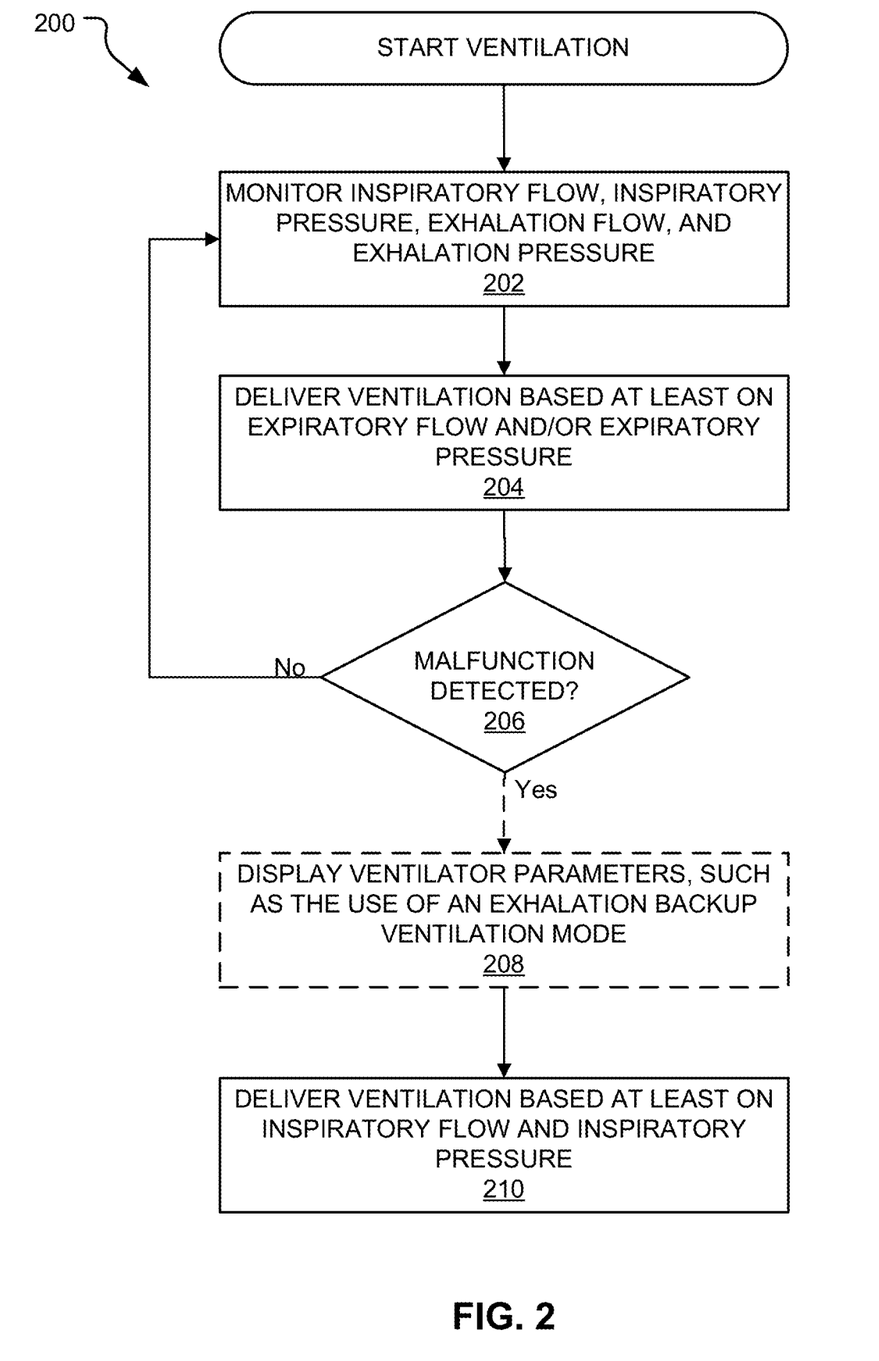
FIG. 2 illustrates an embodiment of a method for ventilation of a patient on a ventilator.

FIG. 2 illustrates an embodiment of a method 200 for ventilating a patient with a ventilator. Further, method 200 provides ventilation after a malfunction is detected that prevents the exhalation pressure and/or exhalation flow from being monitored. The ventilation provided after a malfunction is referred to herein as an exhalation backup-ventilation mode (EBUV). Method 200 begins at the start of ventilation.

As illustrated, method 200 includes a monitoring operation 202. During the monitoring operation 202, the ventilator monitors inspiratory flow, inspiratory pressure, expiratory flow, and expiratory pressure during ventilation of a patient with a ventilator. In some embodiments, the ventilator during the monitoring operation 202 monitors numerous ventilator parameters. As used herein ventilator parameters include any parameter that may be monitored by the ventilator. Sensors suitable for this detection may include any suitable sensing device as known by a person of skill in the art for a ventilator, such as an exhalation flow sensor, expiratory pressure sensor, an inspiratory flow sensor, and an inspiratory pressure sensor.

Further, method 200 also includes a first delivering operation 204. During the first delivering operation 204, the ventilator delivers ventilation based at least on the expiratory flow and/or the expiratory pressure. In some embodiments, the ventilator during the first delivering operation 204 delivers pressure based on the expiratory flow, expiratory pressure, and at least one of inspiratory flow and inspiratory pressure. In some embodiments, the pressure delivered is a pressure limited breath. The pressure delivered during ventilation in based on a breath type and mode of ventilation. In some embodiments, the breath type and/or mode are selected by the clinician. In other embodiments, the mode and/or breath type are determined by the ventilator. Based on the breath type and mode, the ventilator during the first delivering operation 204 may deliver a set pressure or a variable pressure. Further, based on the breath type and mode, the ventilator during first delivering operation 204 may deliver a different pressure during exhalation than delivered during inspiration. For example, the ventilator during first delivering operation 204 may deliver a variable inspiration pressure and set PEEP during exhalation.

Next, method 200 includes a malfunction decision operation 206. During the malfunction decision operation 206, the ventilator determines a malfunction that makes the expiratory flow and/or the expiratory pressure undeterminable. The ventilator during malfunction decision operation 206 determines a malfunction by determining if the exhalation flow sensor, exhalation pressure sensor, and/or the valve command (i.e., a main driver) are unreliable. If the exhalation flow sensor, exhalation pressure sensor, and/or the valve command are determined to be unreliable by the ventilator during malfunction decision operation 206, then the monitored expiratory flow, monitored expiratory pressure, valve position, valve current, valve current command, valve dampening command, and/or etc. may all be unreliable.

The ventilator during malfunction decision operation 206 detects a malfunction. Several different systems and method are currently utilized and known in the art for determining a malfunction in the exhalation module and components of the exhalation module (e.g., the exhalation flow sensor, exhalation pressure sensor, and/or the valve command (i.e., the main driver)). The ventilator during malfunction decision operation 206 may detect malfunction utilizing any of these known systems or methods. For example, malfunctions may be detected based on changes in voltages, temperatures, wattages, coefficients, humidity, and/or overcurrent for various components (e.g., exhalation flow sensor, exhalation valve, and/or main driver) of the exhalation module.

If the ventilator during malfunction decision operation 206 determines a malfunction, the ventilator selects to perform a second delivering operation 210. The performance of the delivering operation 210 ceases the ventilation delivered based at least on the expiratory flow and/or expiratory pressure during first delivery operation 204. In some embodiments, if the ventilator during malfunction decision operation 206 determines a malfunction, the ventilator selects to perform a display operation 208 prior to performing the second delivering operation 210. If the ventilator during malfunction decision operation 206 does not determine a malfunction, the ventilator selects to perform the monitoring operation 202.

Method 200 includes a second delivering operation 210. The ventilator during second delivering operation 210 delivers the ventilation based on at least on the monitored inspiratory flow and the monitored inspiratory pressure. It is understood by a person of skill in the art, that the pressure delivered by the ventilator during the second delivering operation 210 may be based on parameters derived from the inspiratory pressure and inspiratory flow. The ventilation provided to the patient is based on an EBUV mode of ventilation. In some embodiments, the EBUV mode is a pressure targeted mandatory mode of ventilation. The pressure to be administered to a patient during inspiration and exhalation of the mandatory breath is determined by the ventilator during second delivering operation 210. Further, the inspiratory time, and respiratory rate for a patient are also determined by the ventilator during second delivering operation 210. These variables determine the pressure of the gas delivered to the patient during each mandatory breath inspiration and exhalation. The mandatory breaths are administered according to the set respiratory rate by the ventilator during second delivering operation 210. For the EBUV mode, when the inspiratory time is equal to the prescribed inspiratory time, the ventilator during second delivering operation 210 initiates exhalation. Exhalation lasts from the end of inspiration until the next inspiration.

Upon the end of exhalation, another mandatory breath is given to the patient by the ventilator during second delivering operation 210.

In other embodiments, the EBUV mode is a volume-controlled-pressure-targeted (VC+) mandatory mode of ventilation during the second delivering operation 210. The VC+ breath type is a combination of volume and pressure control breath types that may be delivered to a patient as a mandatory breath. In particular, VC+ may provide the benefits associated with setting a target tidal volume, while also allowing for variable flow.

Unlike VC, when the set inspiratory time is reached, the ventilator may initiate exhalation. Exhalation lasts from the end of inspiration until the beginning of the next inspiration. The expiratory time ($T_E$) is based on the respiratory rate set by the clinician. Upon the end of exhalation, another VC+ mandatory breath is given to the patient. By controlling target tidal volume and allowing for variable flow, VC+ allows a clinician to maintain the volume while allowing the flow and pressure targets to fluctuate.

Figure 3:
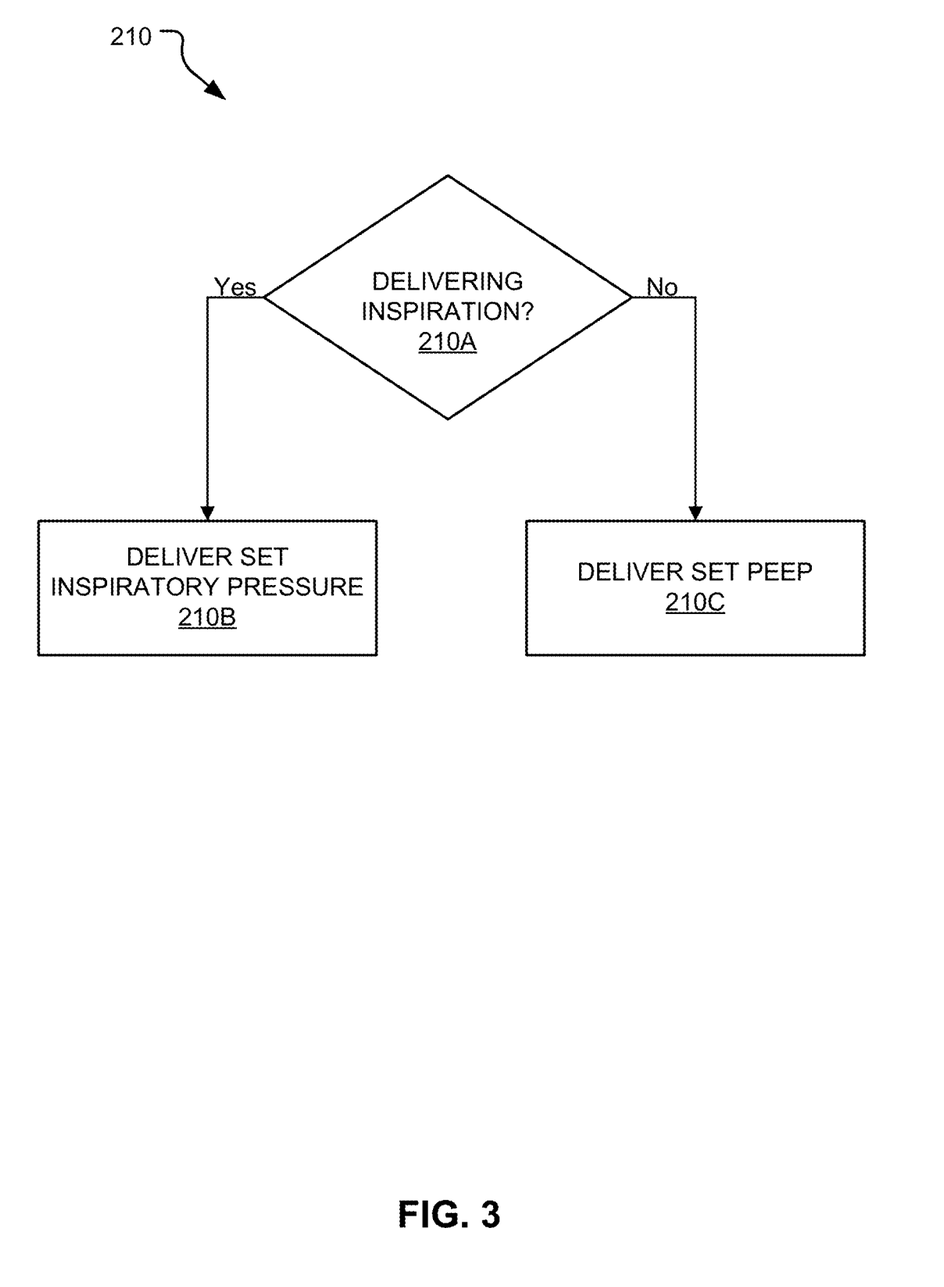
FIG. 3 illustrates an embodiment of a method for delivering a pressure based breath during the method illustrated in FIG. 2.

In some embodiments, the pressure provided by the ventilator during second delivering operation 210 is determined by the phase of the breath. In these embodiments, the method 200 includes an inspiration decision operation 210A as illustrated in FIG. 3. FIG. 3 illustrates an embodiment of a method for delivering a pressure based breath during the method illustrated in FIG. 2. The ventilator during the inspiration decision operation 210A determines if inspiration is being delivered. The ventilator delivers inspiration based on the set inspiratory time and respiration rate. Accordingly, the ventilator determines when inspiration is delivered based on the mandatory mode of ventilation. If the ventilator determines that inspiration is being delivered during inspiration decision operation 210A, the ventilator performs delivering set inspiration pressure 210B. If the ventilator determines that inspiration is not being delivered during inspiration decision operation 210A then exhalation is being delivered and the ventilator performs delivering set PEEP pressure operation 210C.

Figure 4:
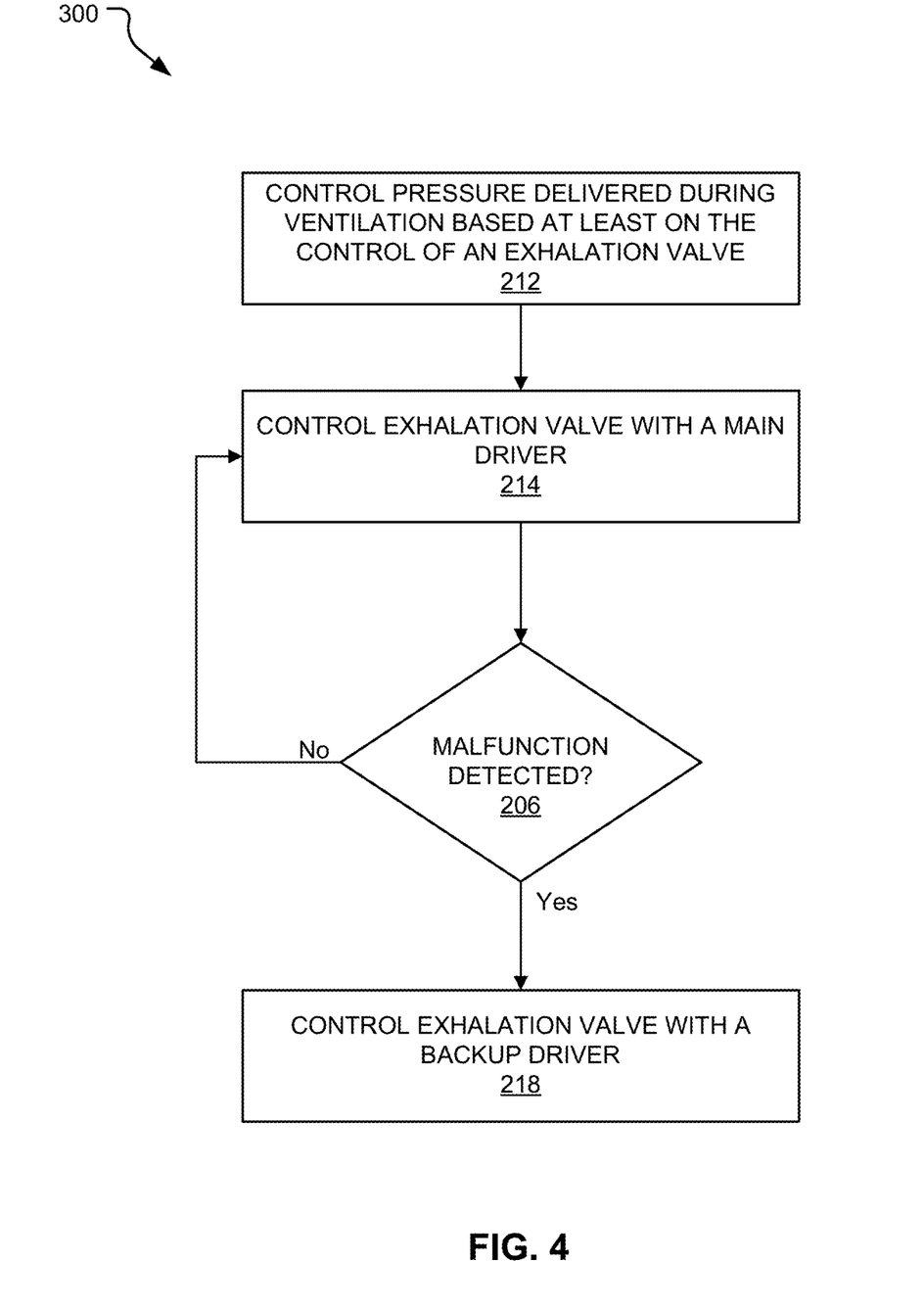
FIG. 4 illustrates an embodiment of a method for delivering a pressure based breath during the method illustrated in FIG. 2.

FIG. 4 illustrates and embodiment of a method 300 for delivering a pressure based breath during the method illustrated in FIG. 2. Method 300 includes a controlling pressure operation 212. The ventilator during controlling pressure operation 212 controls the pressure delivered during ventilation based at least on the control of an exhalation valve. The exhalation valve relieves the over pressure established during inhalation to obtain the desired inspiration pressure during controlling pressure operation 212. Further, the exhalation valve controls establishing the desired PEEP during exhalation during controlling pressure operation 212.

Method 300 further includes a first controlling exhalation valve operation 214. The ventilator during first controlling exhalation valve operation 214 controls the exhalation valve with a main driver. The main driver utilizes a control algorithm that is computed by utilizing monitored exhalation pressure and monitored exhalation flow. The monitored exhalation flow and/or pressure are determined by one or more sensors, such as an exhalation pressure sensor and/or an exhalation flow sensor.

However, during method 300 if a malfunction is detected by the malfunction decision operation 206 during method 200 as described above, the ventilator selects to perform second controlling exhalation valve operation 218. In contrast, during method 300 if a malfunction is not detected by the malfunction decision operation 206 during method 200 as described above, the ventilator selects to continue to perform second controlling exhalation valve operation 218.

As illustrated, method 300 includes a second controlling exhalation valve operation 218. The ventilator during second controlling exhalation valve operation 218 controls the exhalation valve with a backup driver. The malfunction prevents the expiratory flow and expiratory pressure from being determined. Accordingly, the backup driver may utilize a control algorithm that is computed by utilizing monitored inspiratory pressure and monitored inspiratory flow to control the exhalation valve. The monitored inspiratory flow and/or inspiratory pressure are determined by one or more sensors, such as an inspiratory pressure sensor and/or an inspiratory flow sensor. In some embodiments, the backup driver utilizes an inspiration control algorithm to establish the desired inspiration pressure that is computed by utilizing monitored inspiration pressure and monitored inspiration flow. In further, embodiments, the backup driver utilizes an exhalation control algorithm to establish the PEEP that is computed by utilizing monitored inspiration pressure and monitored inspiration flow. In some embodiments, the exhalation control algorithm subtracts the measured inspiration pressure from the desired PEEP. However, because the expiratory pressure is not determinable, the amount of PEEP delivered is determined based on the monitored inspiration pressure and monitored inspiration flow during a malfunction.

In some embodiments, method 200 includes a display operation 208. The ventilator during the display operation 208 displays any suitable information for display on a ventilator. In one embodiment, the ventilator during display operation 208 displays at least one of a detected malfunction, the use of an EBUV mode of ventilation, inspiration pressure, inspiration flow, exhalation pressure, exhalation pressure, delivered pressure, set inspiratory pressure, and/or set PEEP.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2. In some embodiments, this method includes repeatedly performing the steps disclosed in method 200 and method 300 above and/or as illustrated in FIG. 2 and FIG. 3.

In further embodiments, a computer-readable medium having computer-executable instructions for performing a method of ventilating a patient with a ventilator is disclosed. This method includes repeatedly monitoring inspiratory flow, inspiratory pressure, expiratory flow, and expiratory pressure during ventilation of a patient with a ventilator; repeatedly delivering a pressure during ventilation based at least on the expiratory flow and the expiratory pressure; determining a malfunction that makes the expiratory flow and the expiratory pressure undeterminable; and in response to the malfunction, repeatedly delivering the pressure during the ventilation based on the inspiratory flow and the inspiratory pressure.

In some embodiments, the ventilator system includes: means for monitoring inspiratory flow, inspiratory pressure, expiratory flow, and expiratory pressure during ventilation of a patient with a ventilator; means for delivering a pressure during ventilation based at least on the expiratory flow and the expiratory pressure; and means for determining a malfunction that makes the expiratory flow and the expiratory pressure undeterminable; means for in response to the malfunction, delivering the pressure during the ventilation based on the inspiratory flow and the inspiratory pressure.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator, comprising:
    monitoring inspiratory flow, expiratory flow, and expiratory pressure during ventilation of the patient with the ventilator;
    monitoring features associated with at least one of an expiratory flow sensor, an expiratory pressure sensor, and a main driver;
    delivering ventilation for any breath type during a predetermined or a selected mode of ventilation based at least on the expiratory flow and the expiratory pressure, wherein the predetermined or the selected mode of ventilation includes a spontaneous mode, an assist mode, or a mandatory mode;
    determining, with the ventilator, a malfunction in at least one of the expiratory flow sensor, the expiratory pressure sensor, and the main driver that makes at least one of the expiratory flow and the expiratory pressure unreliable based on the features associated with at least one of the expiratory flow sensor, the expiratory pressure sensor, and the main driver;
    in response to the malfunction, automatically ceasing the delivering of the predetermined or the selected mode of ventilation based at least on the expiratory flow and the expiratory pressure and instead automatically delivering an exhalation backup ventilation mode based on at least one of the inspiratory flow and an inspiratory pressure by the ventilator;
    controlling pressure delivered during the ventilation based at least on controlling an exhalation valve;
    controlling the exhalation valve with the main driver;
    in response to the malfunction, controlling the exhalation valve with a backup driver includes:
    inputting the inspiratory flow and the inspiratory pressure during inspiration into an inspiratory control algorithm; and
    inputting the inspiratory flow and the inspiratory pressure during exhalation into an expiratory control algorithm.

2. The method of claim 1, further comprising:
    in response to the malfunction, determining an inspiratory phase;
    wherein the pressure delivered to the patient is a set inspiration pressure during the inspiratory phase.

3. The method of claim 1, further comprising:
    in response to the malfunction, determining an exhalation phase;
    wherein the pressure delivered to the patient is a set PEEP during the exhalation phase.

4. The method of claim 1, wherein the main driver is malfunctioning.

5. The method of claim 4, wherein the exhalation valve relieves an over pressure established during inhalation to obtain a desired inspiration pressure.

6. The method of claim 1, wherein the expiratory control algorithm subtracts the inspiratory pressure from a set PEEP.

7. The method of claim 1, further comprising:
    in response to the malfunction,
    displaying use of the exhalation backup ventilation mode.

8. The method of claim 1, wherein the features include changes in at least one of voltages, temperatures, wattages, coefficients, and humidity.

9. A ventilator system comprising:
    a pressure generating system adapted to generate a flow of breathing gas;
    a ventilation tubing system including a patient interface for connecting the pressure generating system to a patient;
    an exhalation valve connected to the ventilation tubing system;
    a plurality of sensors operatively coupled to at least one of the pressure generating system, the patient, and the ventilation tubing system, wherein the plurality of sensors include an inspiratory pressure sensor for monitoring inspiratory pressure, an inspiratory flow sensor for monitoring inspiratory flow, an expiratory pressure sensor for monitoring exhalation pressure, and an expiratory flow sensor for monitoring expiratory flow;
    a main driver, the main driver controls the exhalation valve to deliver ventilation for any breath type during at least one of an assist mode, a spontaneous mode, and mandatory mode of ventilation to the patient based at least on at least one of the exhalation pressure and the expiratory flow monitored by the plurality of sensors;
    a backup driver, the backup driver controls the exhalation valve to deliver backup ventilation to the patient during an exhalation backup ventilation mode based on at least one of the inspiration pressure and the inspiration flow monitored by the plurality of sensors; and
    a controller, the controller determines a malfunction in at least one of the expiratory flow sensor, the expiratory pressure sensor, and the main driver making the expiratory flow and the expiratory pressure unreliable based on features associated with at least one of the expiratory flow sensor, the expiratory pressure sensor, and the main driver and switches from the main driver to the backup driver in response to the malfunction;

wherein the backup driver controls the exhalation valve during inspiration by utilizing an inspiratory control algorithm; and wherein the backup driver controls the exhalation valve during exhalation by utilizing an exhalation control algorithm.

10. The ventilator system of claim 9, wherein the backup driver is on a circuit isolated from the main driver.

11. The ventilator system of claim 9, wherein the main driver is a differential driver.

12. The ventilator system of claim 9, wherein the backup driver is a pulse modulated driver.

13. The ventilator system of claim 9, further comprising:
a display that displays utilization of the exhalation backup ventilation mode.

14. The ventilator system of claim 9, wherein in response to the malfunction, the controller determines delivery of inspiration and exhalation based on a set inspiratory time and respiration rate;
wherein a pressure delivered to the patient is a set PEEP during exhalation, and
wherein the pressure delivered to the patient is a set inspiration pressure during inspiration.

15. The ventilator system of claim 9, wherein the controller detects the malfunction in the main driver.

16. The ventilator system of claim 9, wherein the expiratory control algorithm subtracts the inspiratory pressure from a set PEEP.

17. The ventilator system of claim 9, wherein the features include changes in at least one of voltages, temperatures, wattages, coefficients, and humidity.

18. The ventilator system of claim 9, wherein the exhalation valve is controlled to relieve an over pressure established during inhalation to obtain a desired inspiration pressure.

19. A ventilatory system, comprising:
at least one processor; and
at least one non-transitory memory, communicatively coupled to the at least one processor and containing instructions that cause the ventilatory system to:
monitor inspiratory flow, inspiratory pressure, expiratory flow, and expiratory pressure during ventilation of a patient based on data from a plurality of sensors;
monitor changes in at least one of voltages, temperatures, wattages, coefficients, and humidity in at least one component of the ventilatory system;
deliver the ventilation for any breath type during at least one of a spontaneous mode, an assist mode, or a mandatory mode of ventilation based at least on the expiratory flow and the expiratory pressure;
determine a malfunction that makes at least one of the expiratory flow and the expiratory pressure unreliable, wherein the malfunction is determined based on the changes;
in response to the malfunction, switching the mode of ventilation from being based at least on the expiratory flow and the expiratory pressure to an exhalation backup ventilation mode that is based on at least one of the inspiratory flow and the inspiratory pressure; and
in response to the malfunction, displaying the malfunction;
controlling a pressure delivered during the ventilation based at least on controlling an exhalation valve;
controlling the exhalation valve with a main driver;
in response to the malfunction, controlling the exhalation valve with a backup driver;
wherein the step of controlling the exhalation valve with the backup driver includes:
inputting the inspiratory flow and the inspiratory pressure during inspiration into an inspiratory control algorithm; and
inputting the inspiratory flow and the inspiratory pressure during exhalation into an expiratory control algorithm.

* * * * *